United States Patent [19]

El-Chahawi

[11] 4,447,644

[45] May 8, 1984

[54] METHOD FOR PREPARATION OF ARYLPYRUVIC ACID

[75] Inventor: Moustafa El-Chahawi, Troisdorf, Fed. Rep. of Germany

[73] Assignee: Dynamit Nobel AG, Troisdorf, Fed. Rep. of Germany

[21] Appl. No.: 381,133

[22] Filed: May 24, 1982

Related U.S. Application Data

[63] Continuation of Ser. No. 223,065, Jan. 7, 1981, abandoned, which is a continuation of Ser. No. 50,028, Jun. 19, 1979, abandoned.

[30] Foreign Application Priority Data

Jun. 26, 1978 [DE] Fed. Rep. of Germany ......... 2828041

[51] Int. Cl.$^3$ ............................................. C07C 51/10
[52] U.S. Cl. ................................................... 562/406
[58] Field of Search ........................................ 562/406

[56] References Cited

U.S. PATENT DOCUMENTS

| | | | |
|---|---|---|---|
| 3,116,306 | 12/1963 | Heck | 562/406 |
| 3,928,429 | 12/1975 | El-Chahawi | 562/406 |
| 4,152,352 | 5/1979 | Perron | 562/406 |
| 4,351,952 | 9/1982 | Foa | 562/406 |

*Primary Examiner*—Michael L. Shippen
*Attorney, Agent, or Firm*—Felfe & Lynch

[57] ABSTRACT

A method for the preparation of optionally substituted arylpyruvic acids by reaction of optionally substituted arylmethylhalides with carbon monoxide in the presence of a metal carbonyl compound and a base is disclosed wherein the base is an alkali metal hydroxide, the process is carried out at a temperature of $-10°$ to $+70°$ C. in the presence of an alcohol or cyclic ether.

6 Claims, No Drawings

METHOD FOR PREPARATION OF ARYLPYRUVIC ACID

This is a continuation application of Ser. No. 223,065 filed Jan. 7, 1981 which is in turn a continuation of Ser. No. 050,028 filed June 19, 1979, both abandoned.

BACKGROUND OF THE INVENTION

1. Field of the Invention

The invention relates to the preparation of optionally substituted arylpyruvic acids by reaction of optionally substituted arylhalogenmethyl compounds with carbon monoxide in an alcohol/water mixture in the presence of metal carbonyls and of an alkali hydroxide.

2. Discussion of the Prior Art

According to J. Anatol. Synthesis 1971, No. 10, pp. 538-39, arylpyruvic acids may be obtained from α-aminonitriles or cyanohydrins from the α-hydroxy-N-tert-carboxylic acid amides by oxidation. This and other synthesis routes require use of starting materials which are not readily available. Moreover, these routes entail numerous intermediate stages or produce only small yields.

In German Auslegeschrift DAS No. 26 00 541 it is proposed to convert arylmethylhalides to arylpyruvic acid with carbon monoxide in the presence of metal carbonyl compounds, particularly cobalt, in the presence of from 1 to 4 mols of alkaline earth bases. This results in a number of undesired by products which render working-up difficult. In column 3, lines 61–64, of that German application, it is expressly stated that arylpyruvic acid will not form when the alkaline-earth bases are replaced with alkali metal bases.

Thus, there has been a need for preparing arylpyruvic acids by simple and economically feasible methods.

SUMMARY OF THE INVENTION

Surprisingly, it has now been found that alkali metal bases are well suited for the preparation of phenylpyruvic acid when a mixture of both an alcohol and water is employed as solvent.

The invention has as its object a method for the preparation of optionally substituted arylpyruvic acids by reaction of optionally substituted arylmethylhalides with carbon monoxide in the presence of a cobalt carbonyl and a basic compound which is characterized by the fact that the reaction is carried out at from −10° to +70° C. in the presence of an alkali metal hydroxide as basic compound.

Chlorides, bromides and, if desired, iodides may be used as arylmethylhalides, chlorides being preferred. As aryl moieties, mono- or binuclear aromatics, which may be substituted in different ways, are used. Preferred substituents are halogens such as fluorine, chlorine, bromine and iodine, alkyl moieties having from 1 to 4 carbon atoms which may be straight-chained or branched, alkoxy or phenoxy groups, which may be substituted or unsubstituted, and nitro, cyano and carbalkoxy groups. The substituents may be present singly or multiply, identically or differently.

Preferred representatives of the arylmethylhalides are benzyl chloride, o, m- and p-chlorobenzyl chloride, o-, m- and p-bromobenzyl chloride, o-, m- and p-fluorobenzyl chloride, o-, m- and p-methylbenzyl chloride, 2,3-dimethyl, 2,4-dimethyl and 3,5-dimethylbenzyl chloride, 1-chloromethylnaphthalene, 2-chloromethylnaphthalene, mono- and dimethoxybenzyl chloride, and o-, m- and p-phenoxybenzyl chloride.

Suited for use as carbonylation catalysts are cobalt carbonyls, preferably dicobalt octacarbonyl, as well as salts such as the potassium or sodium salt of cobalt tetracarbonyl hydride. The catalysts may be added to the reaction mixture as such or in the form of solutions in the solvent of the carbonylation reaction. The molar ratio of metal carbonyl to arylhalogenmethyl compound may range from 1:1 to 1:1000. However, a molar ratio between 1:20 and 1:1000, and preferably between 1:30 and 1:200, is preferred for economical reasons.

The solvents necessary for the reaction are from the group of straight-chain, branched-chain or cyclic alcohols having up to 6 carbon atoms, especially the alkanols, such as methanol, ethanol, propanol, isopropanol, n-butanol, isobutanol, tert-butanol and tert-amyl alcohol. Better results will be obtained as the degree of branching of the alcohols increases. Tertiary alcohols therefore provide very good yields, secondary alcohols provide good yields. However, of the branched alcohols those readily miscible with water are preferred. Definitely preferred as a solvent is tert-butanol.

The weight ratio of arylhalogenmethyl compound to alcohol may range from 1:1 to 1:20.

Suitable basic reagents are alkali hydroxides such as LiOH, NaOH, KOH, and RbOH. Preferred are LiOH and NaOH. The molar ratio of basic reagent to arylhalogenmethyl compound may range from 4:1 to 2:1 and preferably ranges from 2.8:1 to 2.2:1. The bases are advantageously metered in during the reaction in the form of their 5 to 40 weight percent, and preferably 10 to 25 weight percent, solutions.

Aqueous alcoholic solutions may also be used.

The carbon monoxide may be used in the pressure range from 0.5 to 200 bars but is preferably used in the range from 5 to 50 bars. The carbon monoxide may be mixed or contaminated with inert gases such as nitrogen.

The temperature may range from −10° to +70° C. and preferably ranges from 10° to 40° C. It may be necessary to cool during the reaction. Temperatures between +10° and −20° C. may be employed but will give low conversions. In exceptional cases temperatures ranging from 50 to about 70° C. may be used. However, by-products or lower yields of the desired arylpyruvic acids will then be obtained.

The reaction can be performed from 1 up to 4 hours or more. Generally, it is performed for 2 to 3 hours.

Optimum formation of arylpyruvic acids as desired end products is achievable as follows:

Of the alkali hydroxides usable as basic reagents, LiOH yields a very high proportion of arylpyruvic acid, other conditions being equal, while NaOH yields a decidedly lower though still worthwhile proportion thereof. KOH gives a still lower proportion of arylpyruvic acid.

Of the alcohols usable as solvents, tert-butanol in particular, and other tertiary alcohols, will provide a high proportion of arylpyruvic acid. Secondary alcohols such as isopropanol, on the other hand, provide a decidedly lower proportion, and primary alcohols a still lower proportion of arylpyruvic acid.

The highest yields of 90% arylpyruvic acids were observed when LiOH and a tertiary alcohol, and particularly tert-butanol, were used. The reaction temperature then should not be higher than 40° C.

It will be advantageous to add the alkalies necessary for the reaction in accordance with the invention in proportion to the progress of the reaction, as determined from the consumption of carbon monoxide. The catalyst, too, as well as the starting materials may, if desired, be metered in during the reaction.

In general, the reaction will be carried out by first charging the arylhalogenmethyl compound, the alcohol and the metal carbonyl to an autoclave equipped with stirrer under a nitrogen gas atmosphere. Then the requisite carbon monoxide pressure is set. The alkali metal base is then metered in with vigorous stirring. Following this the reaction mixture is filtered, with the alkali salt of arylpyruvic acid being separated as the main component, along with a small amount of alkali salt of arylacetic acid, from the liquid reactants. The filtrate contains the alkali salt of arylacetic acid and, when unbranched alcohols are used, also esters, apart from very small amounts of alkali salt of arylpyruvic acid.

The alkali salts of arylpyruvic acid are acidified with dilute acids such as hydrochloric acid and the bulk of the free acid is isolated. The acidified solution will be found to contain arylacetic acid and arylpyruvic acid, which may be extracted with solvents. Arylacetic acid is readily separable from arylpyruvic acid with benzene or toluene, for example.

The arylpyruvic acid prepared by the method in accordance with the invention are important starting materials for the preparation of α-amino acids such as phenylalanine by reduction of the keto group to the amino group by means of LiB H$_2$CN (R. F. Borch and H. D. Durst: J. Am. Chem. Soc. 91 (1969) 14, p. 3996–97).

During the reaction two moles of carbon monoxide have to be added to each mole of arylmethylhalide in order to get full yealds. The presence of water during the reaction is necessary to form pyruvic acids i.e. to insert two moles of carbon monoxide.

The alkali metal hydroxide should be in homogeneous solution during the reaction. Therefore the amount of the solvent mixture of an alcohol and water should be sufficient to solve the alkali metal hydroxide. Preferrably the alkali metal hydroxide is added in aqueous solution, the alcohol being added seperately, though the alcohol may be added to the aqueous solution or a alcoholic solution of the alkali metal hydroxides may be added and then water may be added seperately.

In order to more fully illustrate the invention and the manner of practicising the same, the following examples are presented:

EXAMPLE 1

2000 g (15.9 mols) of benzyl chloride, 4620 ml of tert-butanol and 60 g (0.18 mol) of $CO_2(CO)_8$ were charged to a 20-liter autoclave under an $N_2$ atmosphere. The autoclave was flushed with CO and brought to a pressure of 20 bars CO. At room temperature, a 9.7 wt. % aqueous LiOH solution was then metered in over a period of 3 hours with constant stirring. The reaction temperature was maintained at under 35° C. It was controlled by reducing the autoclave temperature or reducing the rate of LiOH addition. On completion of CO absorption, the metering in of LiOH was discontinued. (8800 g LiOH as a 9.7 wt. % solution=35 moles). The reaction mixture was forced out of the autoclave with $N_2$ and the solids were separated with a pressure suction filter under $N_2$.

Working up (A) Solids (1) The solids were acidified with 6000 ml of 13 wt. % HCl with stirring. Stirring was continued until the acid has precipitated completely. The phenylpyruvic acid was drawn off by suction, washed with water, and absorbed in ether.

The filtrate remaining after acidification was extracted with ether and combined with the previous ether phase. After the ether had been distilled off, the phenylpyruvic acid was formed into a slurry with a little cold benzene, the phenylacetic acid present being dissolved. 2340 g of phenylpyruvic acid was obtained. The yield was 89.9%.

(2) The benzene was found to contain 21 g of phenylacetic acid. The yield was 0.97%.

(B) Reaction filtrate (1) The reaction filtrate was mixed with $H_2O$ and acidified with HCl. After extraction with ether, the ether phase was repeatedly extracted with a 10% NaOH solution with shaking. The ether was separated and distilled off. The residue was distilled to isolate the neutral carbonylation products.

(2) The NaOH solution was acidified and extracted with ether. Here only phenylacetic acid was obtained, in an amount of 126 g. (Yield, 5.8%)

Total yield of phenylpyruvic acid: 89.9%
Total yield of phenylacetic acid: 6.8%

EXAMPLE 2

The procedure according to Example 1 was followed, except that the temperature was 0° C. and the metering-in time 8 hours. After working up, a conversion of 15.5% was observed. The yield of phenylpyruvic acid was 90% of the reaction product.

EXAMPLE 3

The procedure according to Example 1 was followed, except that the temperature was 20° C. and the metering-in time 6 hours. After working up, a conversion of 95.9% and a yield of phenylpyruvic acid of 87% and of phenylacetic acid of 6% were observed.

EXAMPLE 4

Following the procedure according to Example 1 but using 3800 ml of tert-amyl alcohol in place of tert-butanol, a yield of 39.8% of phenylpyruvic acid and of 12% of phenylacetic acid was obtained.

EXAMPLE 5

Example 1 was repeated, 24 wt. % aqueous NaOH being used, and 35 mols of NaOH being metered in throughout the reaction time.

After working up, a total yield of phenylpyruvic acids of 62.9% and of phenylacetic acid of 33.0% was obtained.

EXAMPLE 6

According to Example 5, but with a temperature of 60° C., 39% phenylpyruvic acid, 33% phenylacetic acid and 2% dibenzyl ketone were obtained.

EXAMPLE 7

Example 1 was repeated, 24 wt. % NaOH and a carbon monoxide pressure of 5 bars being used.

The following total yield was obtained after working up:

Phenylpyruvic acid: 55.7%
Phenylacetic acid: 33.4%
Dibenzyl ketone: 6.1%

EXAMPLE 8

Example 1 was repeated, 24 wt. % NaOH and a carbon monoxide pressure of 100 bars being used.
The total yield after working up was:
Phenylpyruvic acid: 67.9%
Phenylacetic acid: 21.7%

EXAMPLE 9

Example 1 was repeated, 20 wt. % NaOH and a carbon monoxide pressure of 20 bars being used.
The total yield after working up was:
Phenylpyruvic acid: 66.5%
Phenylacetic acid: 21.2%
Benzylphenylpyruvic acid: 3.5%

EXAMPLE 10

The procedure described in Example 1 was followed, except that 22 wt. % KOH and a carbon monoxide pressure of 20 bars were used.
The total yields obtained after working up were:
Phenylpyruvic acid: 50.3%
Phenylacetic acid: 35.4%

EXAMPLE 11

The procedure described in Example 1 was followed, except that 24 wt. % NaOH and a carbon monoxide pressure of 100 bars were used, and that isopropanol was used as solvent.
The total yields obtained after working up were:
Phenylpyruvic acid: 47.1%
Phenylacetic acid: 32.1%
Phenylacetic acid isopropyl ester: 8.7%
Dibenzyl ketone: 6.5%

EXAMPLE 12

The procedure described in Example 1 was followed, except that 24 wt. % NaOH and a carbon monoxide pressure of 100 bars were used, and that ethanol was used as solvent.
The total yields obtained after working up were:
Phenylpyruvic acid: 39.9%
Phenyl acetic acid: 29.6%
Phenylacetic acid ethyl ester: 14.5%
Dibenzyl ketone: 5.1%

EXAMPLE 13

The procedure described in Example 1 was followed, except that 24 wt. % NaOH and a carbon monoxide pressure of 100 bars were used, and that methanol was used as solvent.
The total yields obtained after working up were:
Phenylpyruvic acid: 17.4%
Phenylacetic acid: 48.2%
Phenylacetic acid methyl ester: 21.7%

EXAMPLE 14

The procedure described in Example 1 was followed, except that p-chlorobenzyl chloride was used with 24 wt. % NaOH at a carbon monoxide pressure of 20 bars.
The following total yields were obtained after working up:
p-chlorophenylpyruvic acid: 59.5%
p-chlorophenylacetic acid: 1.1%

EXAMPLE 15

The procedure described in Example 1 was followed, except that p-methylbenzyl chloride was used with 24 wt. % NaOH at a carbon monoxide pressure of 100 bars.
The following total yields were obtained after working up:
p-methylphenylpyruvic acid: 60.8%
p-methylphenylacetic acid: 1.7%

What is claimed is:

1. A process for the preparation of an optionally substituted pyruvic acid comprising contacting an optionally substituted arylmethylhalide with carbon monoxide in the presence of a metal carbonyl, an alkali metal hydroxide and a mixture of a branched chain alcohol and water at $-10°$ to $+70°$ C. while employing at least two mols of carbon monoxide per mol of arylmethylhalide, said branched chain alcohol being selected from the group consisting of tertiary butanol, tertiary amyl alcohol and isopropanol, the reaction mixture consisting essentially of said optionally substituted arylmethylhalide, carbon monoxide, metal carbonyl, alkali metal hydroxide, water and said branched chain alcohol and thereafter acidifying the resultant salt with an acid.

2. A process according to claim 1 wherein said metal carbonyl is cobalt carbonyl.

3. A process according to claim 1, wherein the process is carried out in an amount of a solvent mixture of said alcohol and water sufficient to dissolve the alkali metal hydroxide during the reaction.

4. A process according to claim 1 wherein the alkali metal hydroxide is LiOH.

5. A process according to claim 1 wherein said alcohol is tert. amyl alcohol.

6. A process according to claim 1 wherein said alcohol is a tertiary alcohol.

* * * * *